United States Patent [19]
Allison et al.

[11] Patent Number: 5,205,825
[45] Date of Patent: Apr. 27, 1993

[54] INSERTABLE ELEMENT FOR PREVENTING REUSE OF PLASTIC SYRINGES

[76] Inventors: Alan C. Allison, 233 Marvilla Cir., Pacifica, Calif. 94044; Richard A. Jaffe, 786 Wildwood La., Palo Alto, Calif. 94303

[21] Appl. No.: 732,782

[22] Filed: Jul. 19, 1991

Related U.S. Application Data

[63] Continuation-in-part of Ser. No. 644,465, Jan. 17, 1991, abandoned, which is a continuation of Ser. No. 390,083, Aug. 7, 1989, abandoned.

[51] Int. Cl.$^5$ ............................................. A61M 5/00
[52] U.S. Cl. ..................................... 604/110; 604/220
[58] Field of Search ............... 604/110, 218, 220, 236, 604/238

[56] References Cited

U.S. PATENT DOCUMENTS

| | | |
|---|---|---|
| 3,890,971 | 6/1975 | Leeson et al. . |
| 4,367,738 | 1/1983 | Legendre et al. . |
| 4,391,272 | 7/1983 | Staempfli . |
| 4,493,703 | 1/1985 | Butterfield . |
| 4,731,068 | 3/1988 | Hesse . |
| 4,762,516 | 8/1988 | Luther et al. . |
| 4,781,684 | 11/1988 | Trenner . |
| 4,790,822 | 12/1988 | Haining . |
| 4,961,728 | 10/1990 | Kosinski . |
| 5,000,737 | 3/1991 | Free et al. . |

FOREIGN PATENT DOCUMENTS

| | | |
|---|---|---|
| 8702408 | 3/1989 | PCT Int'l Appl. . |
| 8902287 | 3/1989 | PCT Int'l Appl. . |
| 8801007 | 5/1989 | PCT Int'l Appl. . |

Primary Examiner—C. Fred Rosenbaum
Assistant Examiner—C. Maglione
Attorney, Agent, or Firm—Ostrager & Chong

[57] ABSTRACT

A locking device is capable of being retrofitted by insertion into a standard plastic syringe. The syringe is of the type having a cylindrical inner wall made of plastic material, a closed, distal end, and an open, proximal end for movement of a plunger therein. The plunger has a plunger stem made of plastic material with longitudinal ribs in an "X" shaped cross-section. The locking device has a clip-type body portion formed with a U-shaped channel for clipping onto one longitudinal rib, a first set of barbed points angled toward the plunger stem for engaging the plunger stem when it is depressed toward the distal end after a first retraction movement toward the proximal end of the syringe, and a second set of barbed points angled toward the inner wall of the syringe for engaging the inner wall in order to lock the plunger stem from a second retraction movement, thereby preventing reuse of the syringe. Another spring-type version of the locking device is formed from a single piece of rhombic-shaped sheet metal with an arched spring shape, one pair of barbed points on opposing lateral edges, and another barbed point at a point of the rhombic-shaped metal.

19 Claims, 10 Drawing Sheets

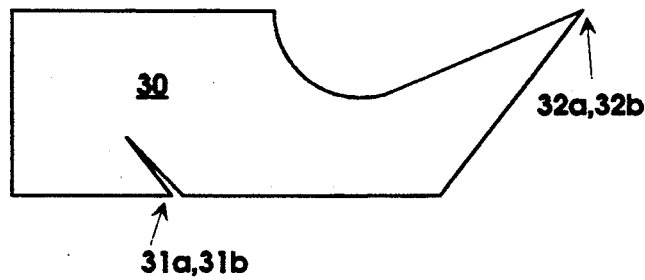
FIG. 4A
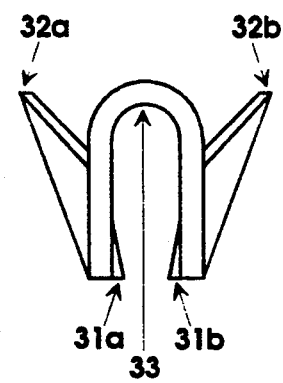
FIG. 4C
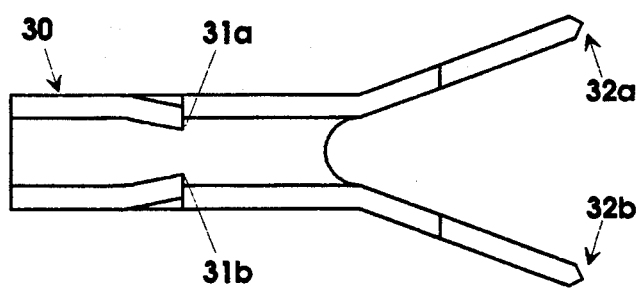
FIG. 4B
FIG. 5
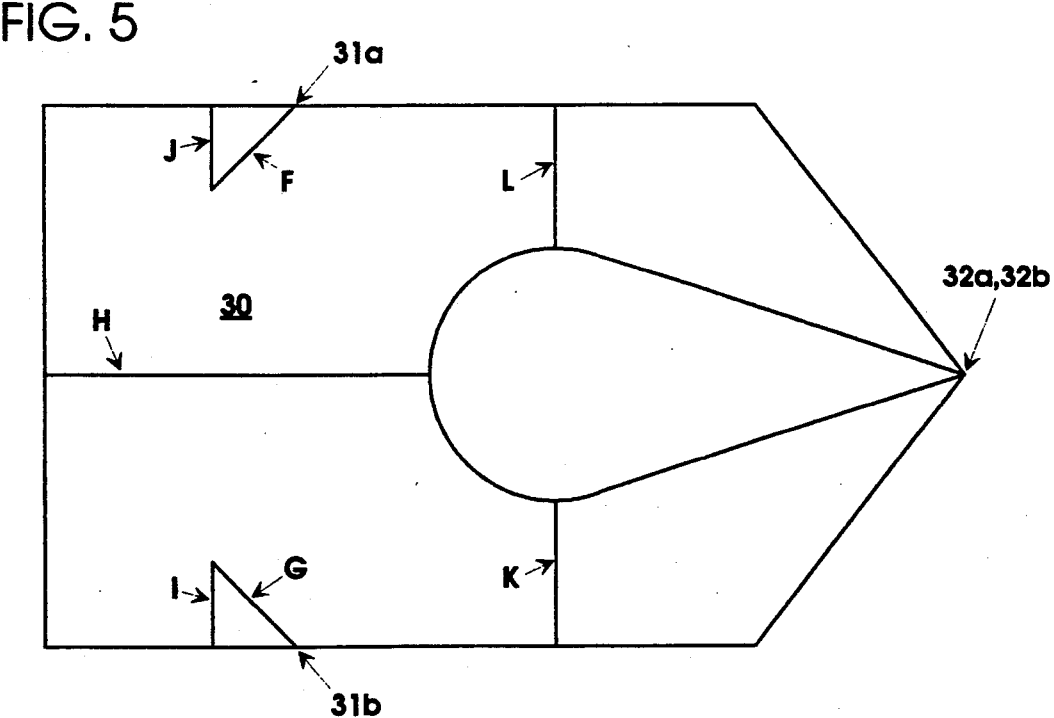

FIG. 6E
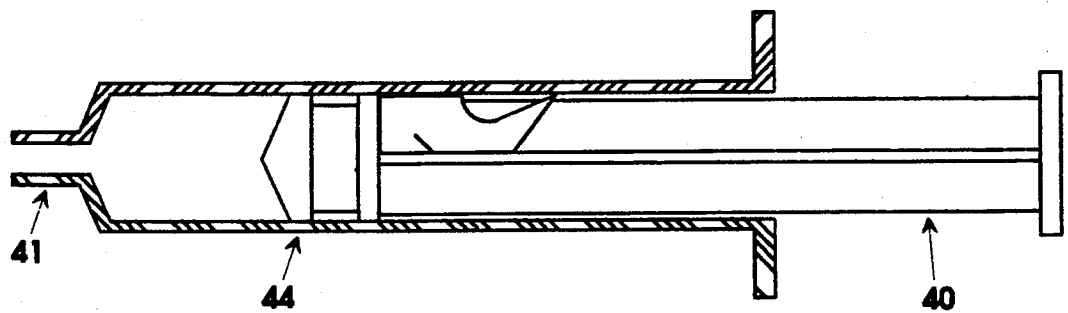
FIG. 6F
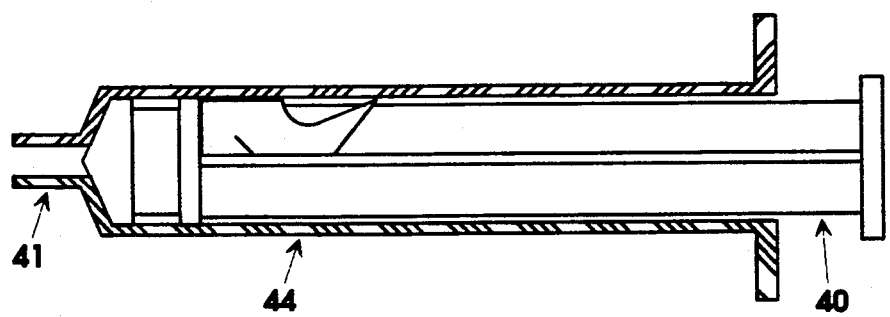
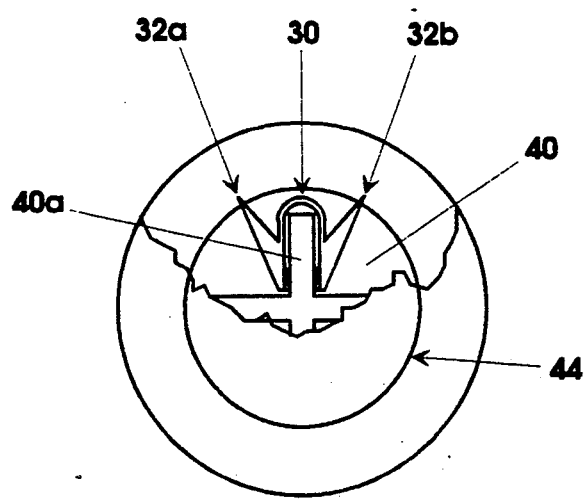
FIG. 6G

FIG. 8A
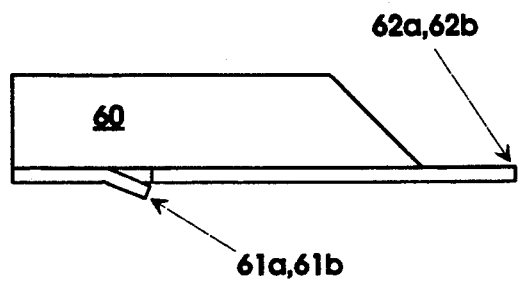
FIG. 8C
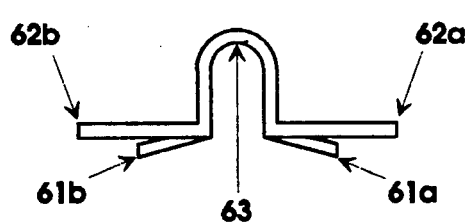
FIG. 8B
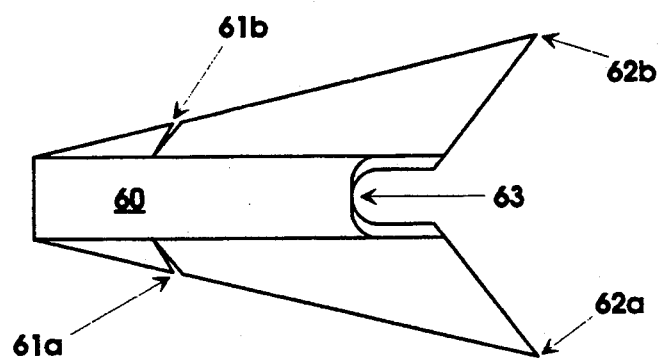
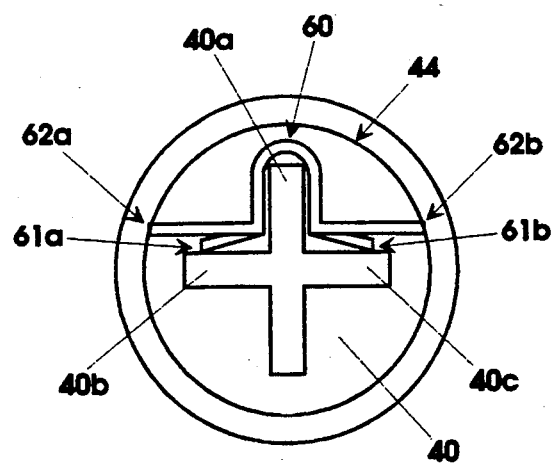
FIG. 8D

FIG. 9A
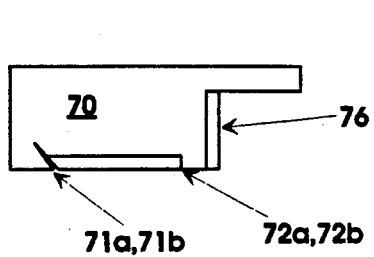
FIG. 9C
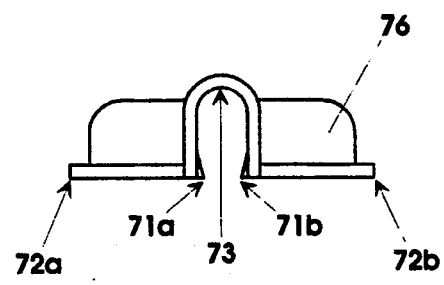
FIG. 9B
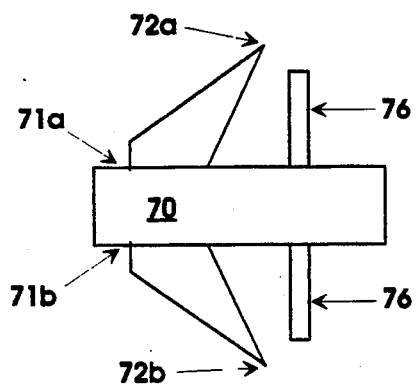
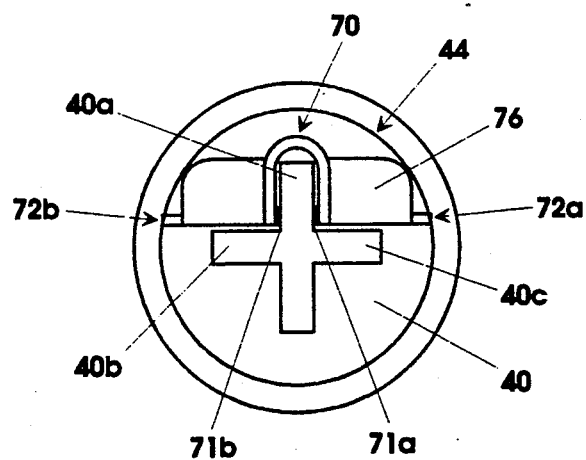
FIG. 9D

INSERTABLE ELEMENT FOR PREVENTING REUSE OF PLASTIC SYRINGES

This is a continuation-in-part of U.S. patent application Ser. No. 07/644,465, filed on Jan. 17, 1991, now abandoned was a continuation of Application No. 07/390,083, filed on Aug. 7, 1989, both of the same title and by the same inventors, now abandoned.

FIELD OF THE INVENTION

This invention generally relates to a device for preventing reuse of a syringe, and more particularly, to one which can be retrofit to or inserted in standard plastic syringes.

BACKGROUND ART

The reuse of needle syringes for intravenous injections has been recognized as a cause of the spread of communicable diseases. Particularly with the current spread of AIDS, it has become desireable to discourage the reuse of unclean syringes. Disposable plastic syringes are widely available because of their low cost and convenience in handling. Although they are intended to be discarded after a single use, they are in fact commonly reused without proper disinfection, particularly in the case of intraveneous drug users.

Prior techniques for preventing reuse of needle syringes include various arrangements for locking out the plunger of a syringe after it has been once loaded and depressed to the end of its travel to inject the contents of the syringe. For example, U.S. Pat. No. 4,731,068 to Hesse discloses a two-part lock construction having a band or sleeve assembled at the injection end of the syringe and dimensioned to be frictionally slidable along the inner wall of the syringe, and a spider element mounted in a fixed position on the plunger and having barb points engaged with the sleeve. When the plunger is first retracted, the spider element and sleeve travel toward the distal end of the syringe together with the plunger. When the plunger is depressed toward the injection end, the sleeve remains at the distal end, through frictional engagement with the inner wall, while the spider element travels toward the injection end with the plunger. If a second attempt is made to retract the plunger, the barbs of the spider element, now exposed to the inner wall in the absence of the sleeve, will engage the inner wall of the syringe and prevent a second retraction.

An alternative arrangement in the Hesse patent has the sleeve slidably supported on the plunger and engaged with the spider element having curved, spring-like prongs assembled at the distal end of the syringe. On the first retraction, the sleeve remains engaged with the spider element, and on the first depression, it is moved toward the injection end to expose the prongs of the spider element. An attempt to retract the plunger the second time will be prevented by engagement of the prongs with the plunger. Other devices, e.g. as shown in U.S. Pat. No. 4,781,684 to Trenner, U.S. Pat. No. 4,493,703 to Butterfield, U.S. Pat. No. 4,391,272 to Staempfli, and U.S. Pat. No. 4,367,738 to Legendre, provide for modifications to the plunger or syringe wall structure which allow only one-way movement of the plunger or which will lock or disable the plunger after a first depression.

Currently, a standard type of widely used disposable plastic syringe has a relatively simple construction of a cylindrical plastic wall formed with a closed injection end and an opposite open end, and a plastic plunger formed with a sealed plunger end, a knob end for depressing, and a stem in between the ends with an "X" shaped cross-section. The prior devices for preventing reuse of a syringe all involve structures which are built-in to the syringe at the time of manufacture. These devices cannot be retrofitted to the type of disposable plastic syringes which are already widely sold and commonly available. Moreover, their specialized construction would depart from that of the standard type of disposable plastic syringe, and would require retooling for manufacture and/or the marketing of a non-standard product.

Some types of lockout elements have been proposed which are insertable into a syringe without requiring modification of the plunger or syringe walls, and therefore can be retrofit into the widely-used type of standard plastic syringes. In the PCT publication of International PCT Application No. PCT/US87/02408 of Michael J. Free, which issued as U.S. Pat. No. 5,000,737 on Mar. 19, 1991, a flute-shaped element is insertable between a pair of adjacent longitudinal ribs of the plunger and the inner syringe wall, and has radially inwardly and outwardly facing sets of points pointing toward the open (proximal) end of the syringe. One set of barbed points engages the plunger ribs and the other engages the syringe walls for the lockout function. However, these types of insertable barbed elements have a tendency to slip from positive locking engagement when force is applied to move the plunger relative to the syringe wall, and/or to be defeated by tampering with the barbed points through the open (proximal) end of the syringe.

SUMMARY OF THE INVENTION

Therefore, it is a principal object of the invention to provide a locking device which can be inserted in a standard disposable plastic syringe and performs its lockout function effectively for preventing reuse of the syringe. Specifically, it is intended that such a locking device positively engage the plunger and syringe walls without slippage and be resistant to tampering through the open end of the syringe.

In accordance with the invention, a locking device is capable of being retrofitted by insertion into a standard plastic syringe. The syringe is of the type having a cylindrical inner wall elongated in the direction of a longitudinal axis thereof and made of a plastic material, a closed, distal end, and an open, proximal end for movement of a plunger therein. The plunger has a plunger stem which extends in the direction of and is movable along the longitudinal axis of the syringe. The plunger stem is made of plastic material and has at least one longitudinal rib formed therewith. The locking device has a clip-type body portion formed with a U-shaped channel for clipping onto the at least one longitudinal rib of the plunger stem, a first set of barbed points spaced apart in a transverse direction perpendicular to the longitudinal axis of the syringe and angled toward the plunger stem facing in the direction toward the proximal end of the syringe for engaging into the plastic material of the plunger stem when the plunger stem is depressed toward the distal end of the syringe after a first retraction movement toward the proximal end of the syringe, and a second set of barbed points spaced apart in the transverse direction and angled toward the inner wall of the syringe facing in the direction toward the proximal end of the syringe for engaging into the plastic material of the syringe inner wall in order to lock the plunger stem from a second retraction movement, thereby preventing reuse of the syringe.

The clip-type body portion allows the locking device to be positively seated by clipping onto the longitudinal rib of the plunger stem, so that it cannot be readily dislodged or displaced from its locking function by tampering. In preferred embodiments, the locking device has an elongated shape, and at least the first set of barbed points is located toward the distal end of the syringe, in order to prevent tampering by deforming or dislodging the barbed points through the open (proximal) end of the syringe. A shield may also be provided at the proximal end of the locking device to block access to the barbed points at the distal end.

Another version of the locking device is formed from a single piece of rhombic-shaped sheet metal which has a longitudinal chord aligned with the longitudinal direction of the syringe, and is bent along a transverse chord to form an arched spring shape. One pair of barbed points is formed by bending back opposing lateral edges on one side of the transverse chord, and another barbed point is formed by a point of the rhombic-shaped sheet metal which is on an opposite side of the transverse chord and aligned with the longitudinal chord. This version has the advantages of being easy to fabricate and providing a positive locking function.

Other objects, features, and advantages of the present invention will become apparent from the following detailed description of the preferred embodiments of the invention considered in conjunction with the drawings, as follows:

DESCRIPTION OF THE DRAWINGS

FIGS. 4A, 4B, and 4C are side, top, and front views, respectively, of a clip-type locking device for insertion in a standard plastic syringe in accordance with the invention;

FIG. 5 is a schematic view illustrating the construction of the barbed element of FIGS. 4A-4C;

FIGS. 6A, 6B, 6C, 6D, 6E, 6F, and 6G illustrate use of the barbed element of FIGS. 4A-4C to prevent reuse of a standard plastic syringe;

FIGS. 8A, 8B, 8C and 8D are side, top, front, and sectional views, respectively, of a third version of a clip-type locking device; and FIGS. 9A, 9B, 9C, 9D, and 9E are views of a fourth version of a clip-type locking device.

DESCRIPTION OF THE PREFERRED EMBODIMENTS

The invention in its broadest sense encompasses a locking device which can be inserted in a standard disposable plastic syringe for preventing its reuse. The locking device operates by the principle of a first set of barbed points which engage in the plastic material of the plunger for holding the device in a fixed position on the plunger stem after it has been once withdrawn (for loading) and depressed, and a second set of barbed points which engage in the plastic material of the inner syringe wall in order to prevent the plunger stem from being withdrawn a second time. In the following description, one spring-type and four clip-type embodiments are illustrated for use with standard plastic syringes. However, it is to be understood that the invention is not limited to these embodiments or types of syringes alone.

Figure 1A:
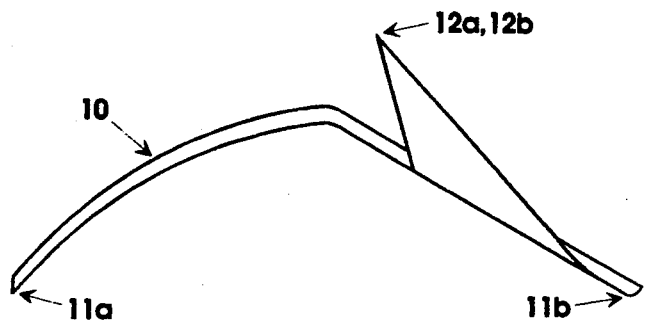
FIGS. 1A, 1B, and 1C are side, top, and front views, respectively, of a spring-type barbed element for insertion in a standard plastic syringe in accordance with the invention.
Figure 1C:
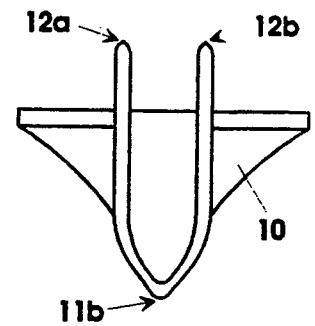
Figure 1B:
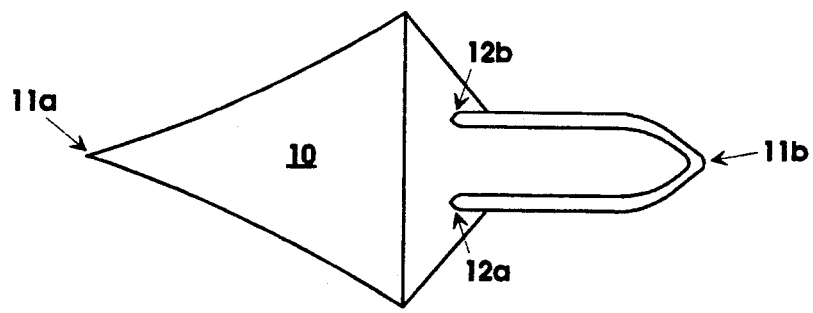

Referring to FIGS. 1A–1C, a spring-type locking device for insertion in a standard plastic syringe has a curved or arched body portion 10 extending in a longitudinal direction which is aligned with the direction of the syringe and plunger stem axis. The body portion 10 has a first set consisting of a single barbed point 11a at one end (toward the left side of the drawing) which faces toward the open (proximal) end of the syringe. At the opposite end (toward the right side of the drawing) in the longitudinal direction, the body portion has a blunted point 11b which faces toward the closed (distal) end of the syringe. The body portion 10 also has a second set consisting of a pair of barbed points 12a, 12b extending outwardly from the body portion 10 and inclined at an angle facing toward the proximal end of the syringe. The points 12a, 12b are spaced apart in a transverse direction (perpendicular to the longitudinal direction) for lateral holding stability. The dimensions and angles of the locking device shown in the drawings correspond to the dimensions (inner bore of syringe, cross-section of plunger, etc.) of a standard plastic syringe of the type manufactured by Becton, Dickinson and Company, of Franklin Lakes, N.J., and sold under the trademark "B-D" in a 5 cc. volumetric size.

Figure 2:
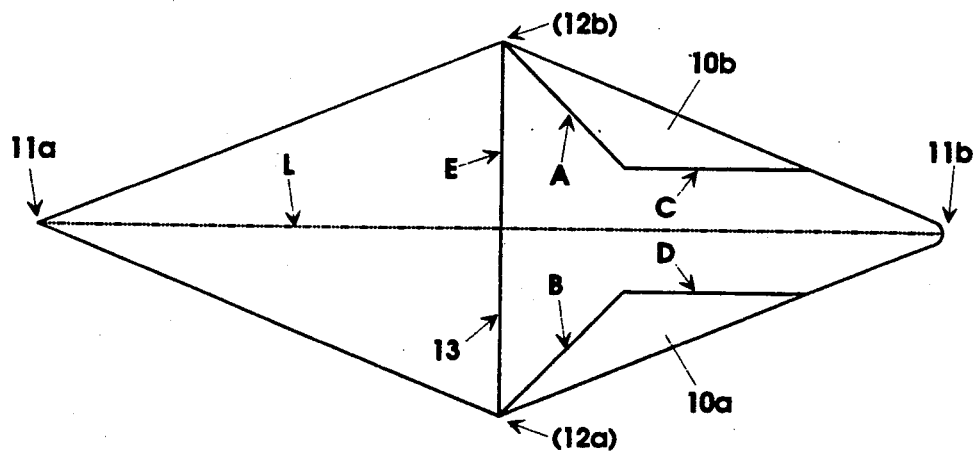
FIG. 2 is a schematic view illustrating the construction of the barbed element of FIGS. 1A-1C.

In FIG. 2, the steps for fabricating the spring-type locking device from a single rhombic-shaped blank are shown. The rhombic-shaped blank is made of sheet metal or other pliable metal, and has a longitudinal chord L and a transverse center chord E. Angled slits A and B are cut in the blank and the cut portions 10a, 10b are bent upward 90 degrees at bend lines C and D such that the barbed points 12a, 12b are formed. The body portion 10 is formed by bending the sections on opposite sides of the center chord E down about 40 degrees along the bend line at E. The barbed device is therefore very simple to fabricate and of low cost.

Figure 3A:
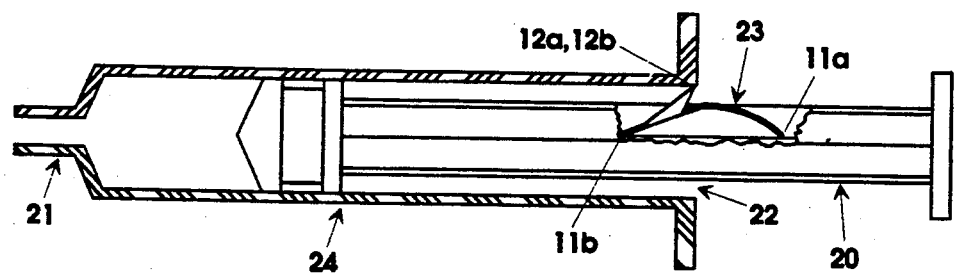
FIGS. 3A, 3b, 3C, 3D, 3E, 3F, and 3G illustrate use of the barbed element of FIGS. 1A-1C to prevent reuse of a standard plastic syringe.

In FIGS. 3A to 3G, the insertion and use of the spring-type barbed element device in a "B-D" type plastic syringe is illustrated. In FIG. 3A, the plunger 20 is partially withdrawn and the barbed device is inserted in the open end 22 of the syringe between two adjacent longitudinal ribs 20a, 20b of the plunger stem. As shown more clearly in FIG. 3G, the plunger stem of the typical plastic syringe has four longitudinal ribs in an X-shaped cross-section, and the barbed device is fitted between two of the ribs 20a, 20b with the barbed point 11a facing toward the open (proximal) end 22, and the blunted point 11b facing toward the injection (distal) end 21. A slight downward force is applied on the arched portion of the barbed device, as indicated by the arrow 23, so that the device can be inserted between the inner surface of the syringe wall 24 and the plunger stem 20 and held therein by a light spring force. The seating of the barbed device between the two longitudinal ribs 20a, 20b with a spring compression force ensures that it will not become dislodged or displaced from the proper position for performing its locking function.

Figure 3B:
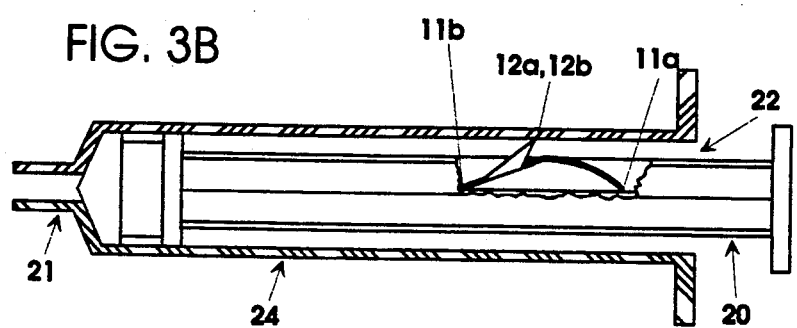
Figure 3C:
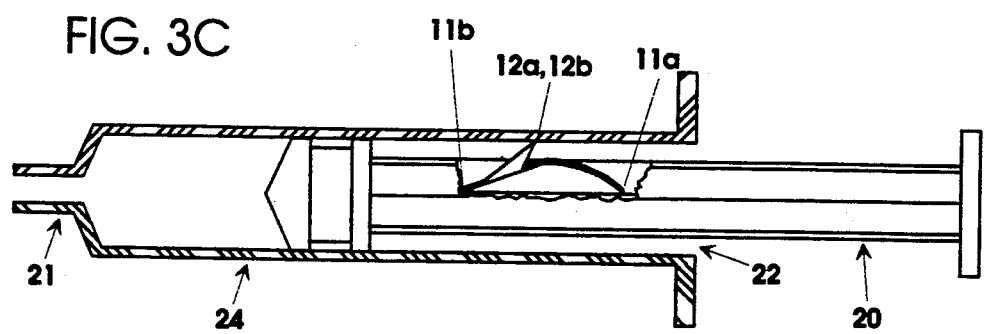
Figure 3D:
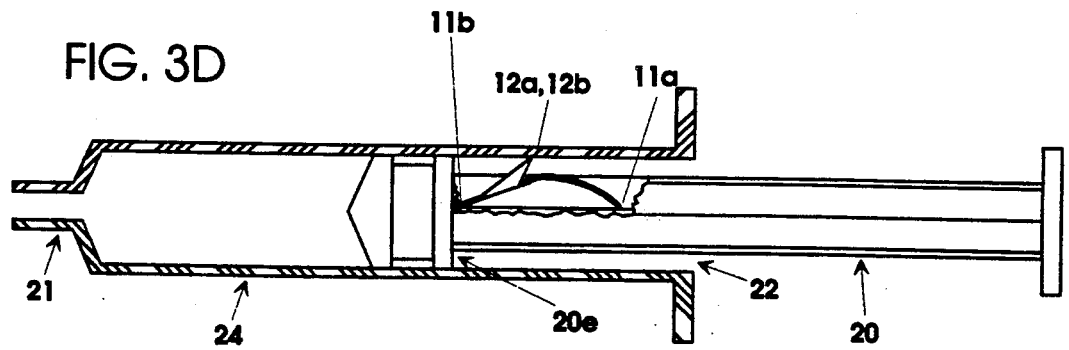

In FIG. 3B, the plunger 20 is shown depressed into the syringe, after the barbed device has been inserted, for packaging or in preparation for later use. The spring compression force holds the locking device so that it remains at the position shown. When the plunger 20 is retracted for the first time for loading of fluid in the expansion volume within the syringe cylindrical wall 24, the barbed device remains at the catch position due to the barbed points 12a, 12b engaging in the plastic material of the syringe wall, while the plunger stem 20 can be smoothly retracted in the direction toward the proximal end 22 since the blunted point 11b rides on the retracting plunger stem and the sharp point 11a remains non-engaged because it is facing in the same direction of retraction. In FIG. 3D, the plunger 20 is fully withdrawn, and the blunted point 11b contacts the injection end 20e of the plunger and prevents further retraction. The spring action of the arched body of the barbed device combined with the force of contact with the plunger end 20e causes positive engagement of the points 11a, 11b in the plastic material of the plunger.

Figure 3E:
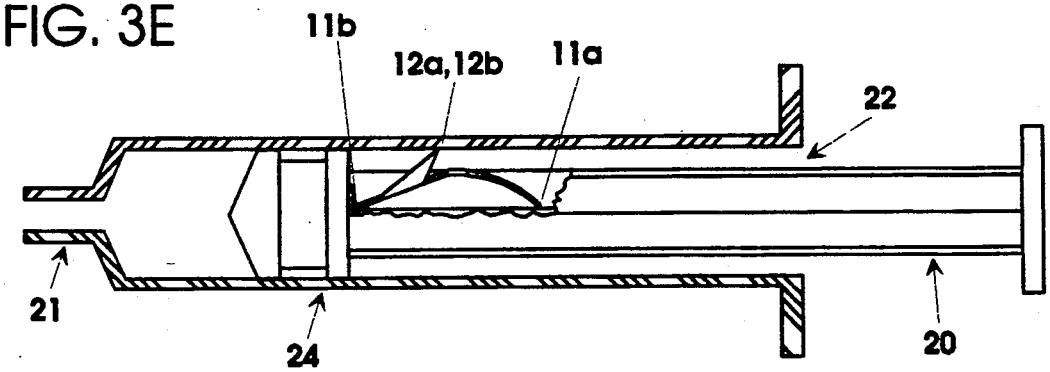
Figure 3F:
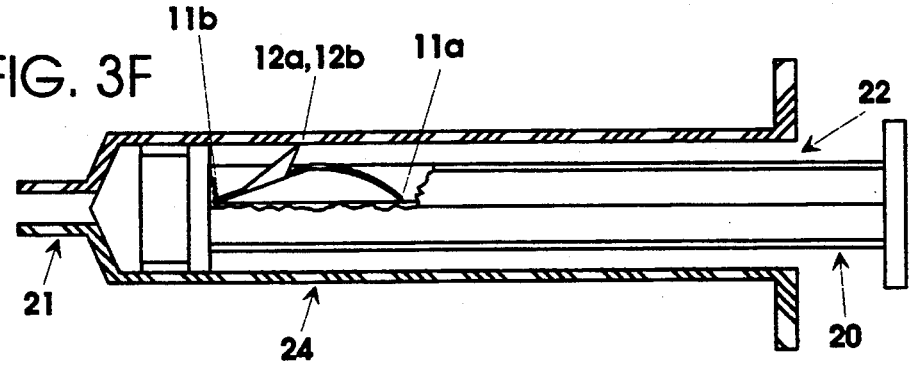
Figure 3G:
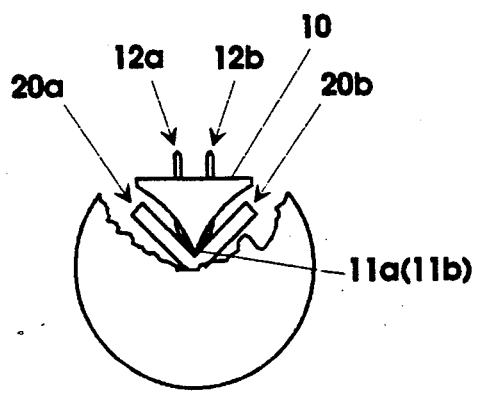

Upon depressing the plunger 20 in an injection movement toward the injection end 21, as shown in FIG. 3E, the locking device is locked in position on the plunger stem by the barbed point 11a engaging in the plastic material of the plunger stem, while the points 12a, 12b ride over the inner surface of the syringe wall 24 due to their being inclined in the opposite direction from the injection end. When the plunger has been fully depressed, in FIG. 3F, the barbed device is located at the injection end of the plunger and is locked in position on the plunger stem by the barbed point 11a, as well as locking the plunger 20 from a second retraction movement (reuse) due to engagement of the barbed points 12a, 12b in the plastic inner wall 24 of the syringe.

Referring to FIGS. 4A-4C, a clip-type locking device is shown having a body portion 30 extending in the longitudinal direction which is formed with a U-shaped channel or recess 33 for fitting onto one longitudinal rib of the X-ribbed plunger stem 20. The body portion 30 has a first pair of barbed points 31a, 31b spaced apart in a transverse direction and angled toward the proximal end of the syringe and facing inwardly toward each other from opposite sides of the U-shaped channel 33 of the body portion 30. A second pair of barbed points 32a, 32b extend outwardly from and above the body portion 30 and are inclined at an angle toward the proximal end and away from the distal (injection) end of the syringe. The points 32a, 32b are spaced apart in the transverse direction for lateral stability. The preferred dimensions and angles shown in the drawings are given for the example of a standard plastic syringe sold under the trademark "Monoject" of a 3 cc. volumetric size.

In FIG. 5, the steps for fabricating the clip-type locking device from a single blank of metal are shown. Angled slits F and G are cut in the blank and the cut portions are bent slightly downward (to face inward) along the bend lines I and J to form the first set of barbed points 31a, 31b. The body portion 30 and channel 33 are formed by bending the opposing sides curvedly along longitudinal bend line H. The second set of barbed points 32a, 32b are formed by cutting out an oval shaped portion at the proximal end and separating the tips.

Figure 6A:
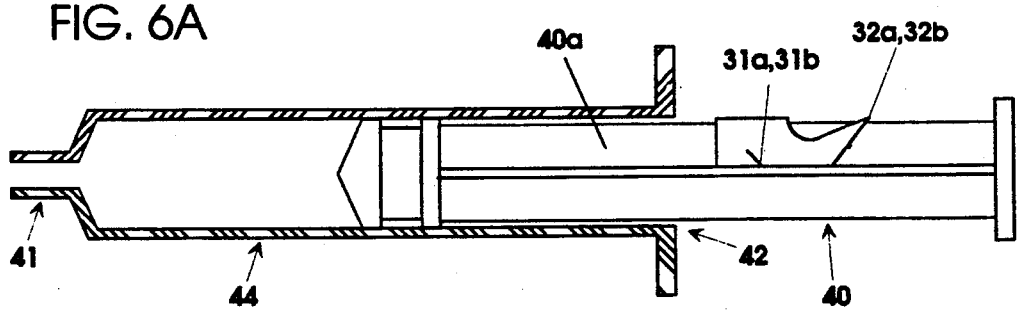

In FIGS. 6A to 6G, the insertion and use of the clip-type barbed insertable device in a "Monoject" type of plastic syringe is illustrated. In FIG. 6A, the X-ribbed plunger 40 is partially withdrawn and the barbed device is loaded therein by snap-fitting the U-shaped channel 33 onto one longitudinal rib 40a of the plunger stem, as shown more clearly in FIG. 6G, with both sets of barbed points 31a, 31b and 32a, 32b facing toward the proximal end 42 and away from the injection end 41 of the syringe. The barbed device is held in place by the clipping force of the U-shaped channel on the longitudinal rib 40a of the plunger stem.

Figure 6B:
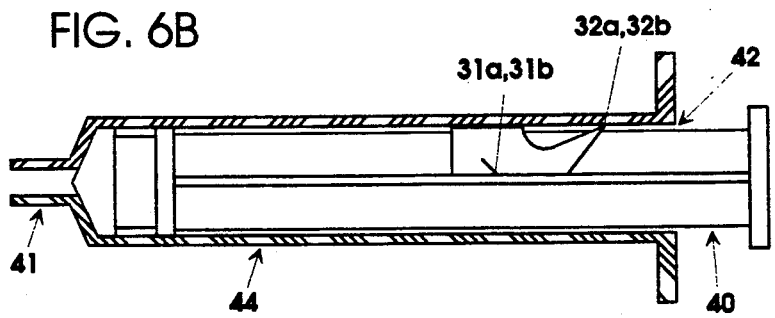
Figure 6C:
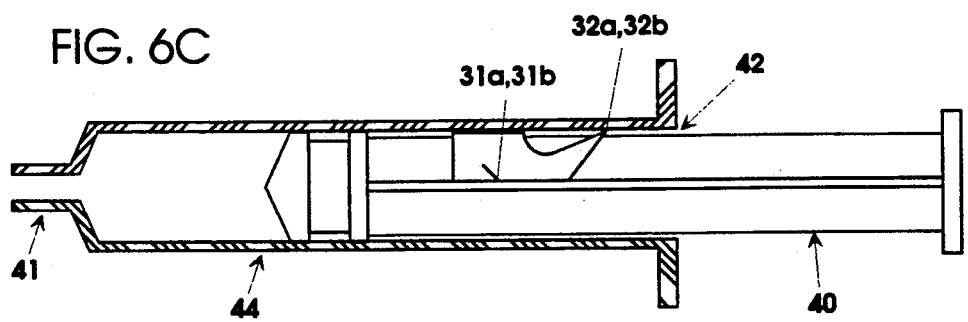
Figure 6D:
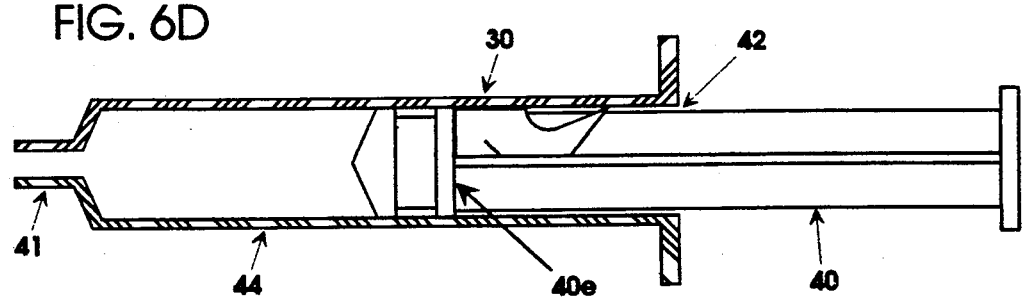
Figure 7A:
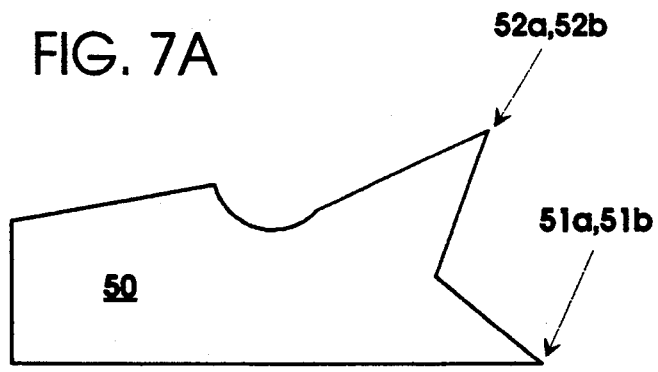
FIGS. 7A, 7B, 7C and 7D are side, top, front, and sectional views, respectively, of another version of a clip-type locking device.
Figure 7C:
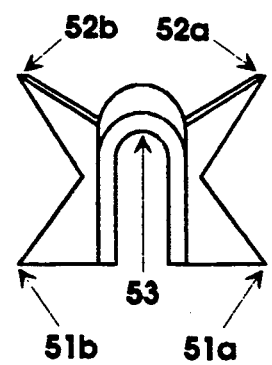
Figure 7B:
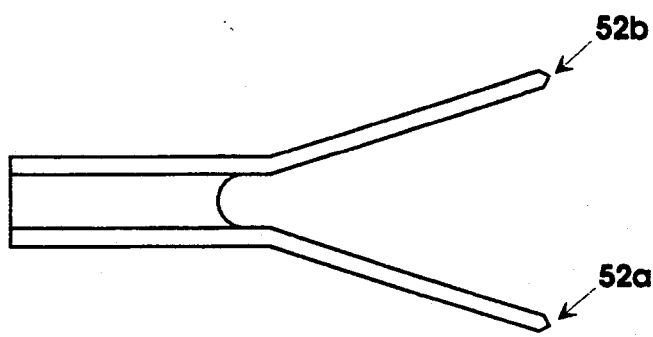
Figure 7D:
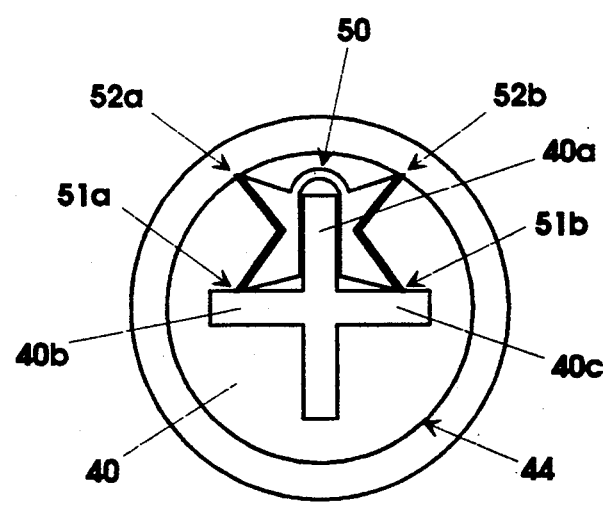

In FIG. 6B, the plunger 40 is depressed into the syringe and the device is held in the catch position on the plunger stem by the points 31a, 31b becoming engaged in the plastic material of the plunger stem. When the plunger is retracted for loading of fluid in the syringe cylinder, in FIG. 6C, the barbed device remains at the catch position due to the second set of barbed points 32a, 32b becoming engaged in the syringe wall 44, while the first set of barbed points 31a, 31b ride over the retracting plunger stem. In FIG. 6D, the plunger is fully withdrawn, and the back end of the device 30 contacts the injection end 40e of the plunger and prevents further retraction. The force of contact with the plunger end 40e drives the points 32a, 32b into deeper engagement in the plastic material to prevent further retraction.

Upon depressing the plunger in an injection movement toward the injection end 41, as shown in FIG. 6E, the barbed device becomes locked in position on the plunger stem by the first set of barbed points 31a, 31b engaging in the longitudinal rib 40a of the plunger stem, while the second set of barbed points 32a, 32b ride over the inner surface of the syringe wall 44 due to their being inclined in the proximal direction away from the injection end. When the plunger has been fully depressed, in FIG. 6F, the barbed device is located at the injection end of the plunger and is locked in position on the plunger stem by the points 31a, 31b, as well as locking the plunger stem 40 from a further retraction movement (reuse) by engagement of the barbed points 32a, 32b in the syringe wall.

The invention is particularly advantageous in that the barbed device can be fabricated readily and inexpensively, and can be retrofitted to or assembled with the standard types of disposable plastic syringes that are currently in wide use. The arrangement of barbed points allows a first retraction of the plunger for loading the injection fluid, but positively prevent a second retraction through engagement in the plastic material of the plunger stem and syringe wall, thereby locking the syringe from reuse. Thus, the invention can be immediately adopted for use in the widely used types of standard plastic syringes, thereby contributing to prevention of the spread of blood-transmitted diseases, such as AIDS.

Another clip-type version of the locking device is shown in FIGS. 7A to 7D having an elongated body portion 50 formed with a U-shaped channel 53, a first set of barbed points 51a, 51b, and a second set of barbed points 52a, 52b. In contrast to the embodiment in FIGS. 4A to 4C, wherein the first and second sets of barbed points are located at opposite ends of the body portion, i.e., toward the distal and proximal ends of the syringe, respectively, the embodiment in FIGS. 7A to 7D have both sets of points located toward the proximal end of the elongated body portion 50. As shown more clearly in FIG. 7D, the first set of points 51a, 51b engage in the adjacent longitudinal ribs 40b, 40c on each side of the longitudinal rib 40a, while the second set of points 52a, 52b are angled upwards to engage in the syringe wall 44.

A third clip-type version of the locking device is shown in FIGS. 8A to 8D having an elongated body portion 60 formed with a U-shaped channel 63, a first set of barbed points 61a, 61b, and a second set of barbed points 62a, 62b. As in the embodiment in FIGS. 4A to 4C, this embodiment has both sets of points located at opposite ends of the body portion 60, i.e., toward the distal and proximal ends of the syringe, respectively. As shown in FIG. 8D, the first set of points 61a, 61b engage in the adjacent longitudinal ribs 40b, 40c on each side of the longitudinal rib 40a, while the second set of points 62a, 62b lie in substantially the same plane and engage in portions of the syringe wall 44 adjacent the longitudinal ribs 40b, 40c.

A fourth clip-type version of the locking device is shown in FIGS. 9A to 9D having an elongated body portion 70 formed with a U-shaped channel 73, a first set of barbed points 71a, 71b, and a second set of barbed points 72a, 72b. As a tamper-proof measure, this embodiment has both sets of points located toward the distal end of the syringe and a shield 76 extends from the body portion toward the proximal end of the syringe. As shown in FIG. 9D, the first set of points 71a, 71b engage in the adjacent longitudinal ribs 40b, 40c on each side of the longitudinal rib 40a, while the second set of points 72a, 72b lie in substantially the same plane and engage in portions of the syringe wall 44 adjacent the longitudinal ribs 40b, 40c. The shield 76 blocks access to both sets of points through the open end of the syringe. The shield can be formed from a single blank by undercutting and bending back portions from the proximal end of the body portion.

When syringes are used illegally for sharing of intravenous drugs, the illegal user may attempt various ways to defeat a locking device. One method of defeating a locking device in a syringe is by dislodging or displacing the locking element to a dysfunctional position. For example, the flute-type device in the Free U.S. Pat. No. 5,000,737, as well as other types of devices which rely on a spring force between the syringe wall and plunger stem to position the first and second sets of points, can be dislodged or displaced by retracting the plunger with excessive force the first time, so that the device becomes too deeply embedded in the syringe wall to maintain contact between the other set of points and the plunger stem. Devices which rely on a spring force can also be defeated by pressing the device upward with a long tool inserted through the open end of the syringe and deforming it against the syringe wall. Moreover, devices which have both sets of points located at the proximal end can be defeated by deforming one or both sets of barbed points so that they cannot perform their lockout function.

Figure 9E:
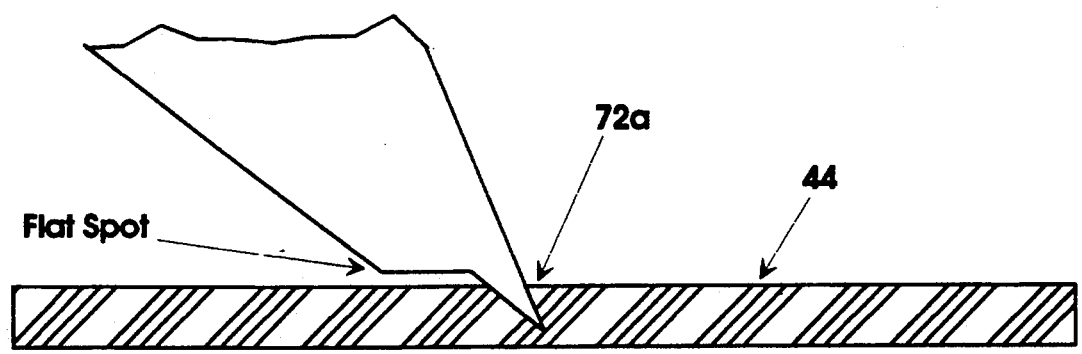

In the above-mentioned clip-type embodiments of the invention, the clip-type body portion clips snugly onto the longitudinal rib of the plunger stem and cannot be readily dislodged or deformed by retracting with excessive force or by pressing upwards with a tool. The first and second sets of points are independent of each other and do not rely on maintenance of a spring force between the plunger stem and syringe wall for proper engagement of the points. Moreover, in the first and third clip-type embodiments, the first set of barbed points for engagement with the plunger stem cannot be readily deformed or dislodged because they are located on the distal end of the device where they cannot be reached by a tool inserted at the proximal end. The second set of points, being angled outward over a greater radial extent are more difficult to deform away from contact with the syringe wall. In the fourth clip-type embodiment, both sets of barbed points are located at the distal end of the device and the shield blocks access to them, so that neither set can be tampered with easily by a tool inserted at the proximal end. Also, the barbed points may be provided with a flat spot, as shown in FIG. 9E, to limit the depth of penetration of the second set of barbed points into the syringe wall when the plunger is first retracted. This prevents the locking device from becoming unseated by retracting the plunger with excessive force.

Numerous modifications and variations are of course possible in light of the principles of the invention disclosed above. For example, the orientation and arrangement of the barbed points and the holding structure of the body portion of the barbed element may be modified readily. All such modifications and variations are intended to be included within the entire spirit and scope of the invention, as defined in the following claims.

We claim:

1. A locking device, capable of being retrofitted by insertion into a plastic syringe, wherein the syringe is of the type having a cylindrical inner wall elongated in the direction of a longitudinal axis thereof and made of a plastic material; a closed, distal end, and an open, proximal end for movement of a plunger thereon, the plunger having a plunger stem which extends in the direction of and is movable along the longitudinal axis of the syringe, the plunger stem being made of plastic material and having at least one longitudinal rib formed therewith, said locking device comprising:

a clip-type body portion formed of a compact size and shape to allow its insertion through the open end of the syringe between the plunger stem and the inner wall of the syringe, and having a U-shaped channel for clipping onto the at least one longitudinal rib of the plunger stem, said clip-type body portion of said locking device being formed with a first set of barbed points spaced apart in a transverse direction perpendicular to the longitudinal axis of the syringe and angled toward the plunger stem facing in the direction toward the proximal end of the syringe for engaging into the plastic material of the plunger stem when the plunger stem is depressed toward the distal end of the syringe after a first retraction movement toward the proximal end of the syringe, and a second set of barbed points spaced apart in the transverse direction and angled toward the inner wall of the syringe facing in the direction toward the proximal end of the syringe for engaging into the plastic material of the syringe inner wall in order to lock the plunger stem from a second retraction movement, thereby preventing reuse of the syringe.

2. A locking device according to claim 1, wherein the plunger stem has four longitudinal ribs in an "X" shaped cross-section, and said first set of barbed points are angled inwardly toward each other so as to engage in the one longitudinal rib on which said locking device is clipped.

3. A locking device according to claim 1, wherein the plunger stem has four longitudinal ribs in an "X" shaped cross-section, and said first set of barbed points are angled outwardly away from each other so as to engage in a pair of adjacent longitudinal ribs on respective sides of said one longitudinal rib on which said locking device is clipped.

4. A locking device according to claim 1, wherein the plunger stem has four longitudinal ribs in an "X" shaped cross-section, and said second set of barbed points are angled radially outwardly so as to engage in the inner wall of the syringe adjacent to and on opposite sides of said one longitudinal rib on which said locking device is clipped.

5. A locking device according to claim 1, wherein the plunger stem has four longitudinal ribs in an "X" shaped cross-section, and said second set of barbed points are angled radially outwardly and lie in parallel with a plane defined by a pair of adjacent longitudinal ribs on respective sides of said one longitudinal rib on which said locking device is clipped, so as to engage in the inner wall of the syringe adjacent said pair of longitudinal ribs.

6. A locking device according to claim 1, wherein said clip-type body portion has an elongated shape, and at least one of said first and second sets of barbed points is located at an end of said elongated clip-type body portion disposed toward the distal end of the syringe.

7. A locking device according to claim 6, wherein said first set of barbed points is located at the end of said clip-type body portion facing toward the distal end of the syringe, and said second set of barbed points is located at an opposite end of said clip-type body portion facing toward the proximal end of the syringe.

8. A locking device according to claim 6, wherein both of said first and second sets of barbed points are located at the end of said clip-type body portion facing toward the distal end of the syringe.

9. A locking device according to claim 8, wherein said clip-type body portion includes a shield affixed thereto and located on an end thereof disposed toward the proximal end of the syringe for blocking access to said sets of barbed points located toward the distal end through the open, proximal end of the syringe.

10. A locking device according to claim 1, wherein at least said second set of barbed points are formed with flat spots for limiting their depth of penetration into the syringe inner wall.

11. A syringe with a locking device inserted therein for preventing its reuse, said syringe comprising:
a cylindrical inner wall elongated in the direction of a longitudinal axis thereof and made of a plastic material, a closed, distal end, and an open, proximal end for movement of a plunger therein,
a plunger having a plunger stem which extends in the direction of and is movable along the longitudinal axis of the syringe, the plunger stem being made of plastic material and having at least one longitudinal rib formed therewith, and
a locking device having a clip-type body portion formed of a compact size and shape to allow its insertion through the open end of the syringe between the plunger stem and the inner wall of the syringe, and having a U-shaped channel for clipping onto the at least one longitudinal rib of the plunger stem,
said clip-type body portion of said locking device being formed with a first set of barbed points spaced apart in a transverse direction perpendicular to the longitudinal axis of the syringe and angled toward the plunger stem facing in the direction toward the proximal end of the syringe for engaging into the plastic material of the plunger stem when the plunger stem is depressed toward the distal end of the syringe after a first retraction movement toward the proximal end of the syringe, and a second set of barbed points spaced apart in the transverse direction and angled toward the inner wall of the syringe facing in the direction toward the proximal end of the syringe for engaging into the plastic material of the syringe inner wall in order to lock the plunger stem from a second retraction movement, thereby preventing reuse of the syringe.

12. A syringe according to claim 11, wherein the plunger stem has four longitudinal ribs in an "X" shaped cross-section, and said first set of barbed points are angled inwardly toward each other so as to engage in the one longitudinal rib on which said locking device is clipped.

13. A syringe according to claim 11, wherein the plunger stem has four longitudinal ribs in an "X" shaped cross-section, and said first set of barbed points are angled outwardly away from each other so as to engage in a pair of adjacent longitudinal ribs on respective sides of said one longitudinal rib on which said locking device is clipped.

14. A syringe according to claim 11, wherein the plunger stem has four longitudinal ribs in an "X" shaped cross-section, and said second set of barbed points are angled radially outwardly so as to engage in the inner wall of the syringe adjacent to and on opposite sides of said one longitudinal rib on which said locking device is clipped.

15. A syringe according to claim 11, wherein the plunger stem has four longitudinal ribs in an "X" shaped cross-section, and said second set of barbed points are angled radially outwardly and lie in parallel with a plane defined by a pair of adjacent longitudinal ribs on respective sides of said one longitudinal rib on which said locking device is clipped, so as to engage in the inner wall of the syringe adjacent said pair of longitudinal ribs.

16. A syringe according to claim 11, wherein said clip-type body portion has an elongated shape, and at least one of said first and second sets of barbed points is located at an end of said elongated clip-type body portion disposed toward the distal end of the syringe.

17. A syringe according to claim 16, wherein said first set of barbed points is located at the end of said clip-type body portion facing toward the distal end of the syringe, and said second set of barbed points is located at an opposite end of said clip-type body portion facing toward the proximal end of the syringe.

18. A syringe according to claim 16, wherein both of said first and second sets of barbed points are located at the end of said clip-type body portion facing toward the distal end of the syringe.

19. A syringe according to claim 18, wherein said clip-type body portion includes a shield affixed thereto and located on an end thereof disposed toward the proximal end of the syringe for blocking access to said sets of barbed points located toward the distal end through the open, proximal end of the syringe.

* * * * *